(12) United States Patent
Takino et al.

(10) Patent No.: US 9,259,366 B2
(45) Date of Patent: Feb. 16, 2016

(54) DISPOSABLE WEARING ARTICLE

(71) Applicant: Unicharm Corporation, Ehime (JP)

(72) Inventors: Shunsuke Takino, Kagawa (JP);
Katsufumi Aoki, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/386,947

(22) PCT Filed: Mar. 27, 2013

(86) PCT No.: PCT/JP2013/059136
§ 371 (c)(1),
(2) Date: Sep. 22, 2014

(87) PCT Pub. No.: WO2013/146946
PCT Pub. Date: Oct. 3, 2013

(65) Prior Publication Data
US 2015/0080829 A1     Mar. 19, 2015

(30) Foreign Application Priority Data

Mar. 30, 2012  (JP) ................................. 2012-081724

(51) Int. Cl.
*A61F 13/62* (2006.01)
*A61F 13/551* (2006.01)

(52) U.S. Cl.
CPC ........... *A61F 13/622* (2013.01); *A61F 13/5512* (2013.01)

(58) Field of Classification Search
CPC ............... A61F 13/56; A61F 13/5512; A61F 2013/5666; A61F 13/5622; A61F 13/62; A61F 13/66; A61F 2013/5683; A61F 2013/5694; A61F 13/565

USPC ........................................ 604/385.01, 385.13
See application file for complete search history.

(56) References Cited

U.S. PATENT DOCUMENTS 6,264,644 B1    7/2001  Igaue et al.
7,765,614 B2 *  8/2010  Takino et al. ..................... 2/111
(Continued)

FOREIGN PATENT DOCUMENTS

EP    1 541 105 A1    6/2005
EP    1 552 801 A1    7/2005
(Continued)

OTHER PUBLICATIONS

International Search Report from corresponding PCT application No. PCT/JP2013/059136 dated May 7, 2013 (4 pgs).
(Continued)

*Primary Examiner* — Michele M Kidwell
(74) *Attorney, Agent, or Firm* — Brinks Gilson & Lione (57) ABSTRACT

A disposable wearing article including a tape tab being capable of fix the used disposable wearing article by a simple handling. The disposable diaper includes a chassis, an absorbent structure attached to a skin-contact surface of the chassis and a tape tab attached to a non-skin-contact surface. The tape tab is attached to a rear waist sheet and folded back so as to define a first section, a second section and a third section. The first section is provided with a mechanical fastener which is substantially not retained on the second section. Outside in the longitudinal direction of a fastening portion provided with the mechanical fastener, first temporary joint spots for temporarily joining part of the first and second sections and second temporary joint spots for temporarily joining part of the first through third sections are provided.

20 Claims, 7 Drawing Sheets

(56) References Cited

U.S. PATENT DOCUMENTS 7,771,405 B2 * 8/2010 Andersson et al. ...... 604/385.06
7,867,208 B2 * 1/2011 Samuelsson et al. .... 604/385.13

FOREIGN PATENT DOCUMENTS

| JP | 6-77718 | 11/1994 |
| JP | 08-239635 | 9/1996 |
| JP | 10-071172 | 3/1998 |
| JP | 10-137008 | 5/1998 |
| JP | 2001-178777 | 7/2001 |
| WO | WO 00/27328 | 5/2000 |
| WO | WO 2008/156931 A1 | 12/2008 |

OTHER PUBLICATIONS

European supplementary Search Report from corresponding European application No. 13769219.0 dated Aug. 11, 2015 (7 pgs).

* cited by examiner

DISPOSABLE WEARING ARTICLE

RELATED APPLICATION

This application is a 35 U.S.C. §371 national phase filing of International Patent Application No. PCT/JP2013/059136, filed Mar. 27, 2013, through which and to which priority is claimed under 35 U.S.C. §119 to Japanese Patent Application No. 2012-081724, filed Mar. 30, 2012.

TECHNICAL FIELD

The present invention relates to disposable wearing articles and more particularly to disposable wearing articles, for example, disposable diapers, disposable toilet-training pants, disposable incontinent pants, disposable sanitary pants and disposable absorbent pads each of them including a tape tab used to roll up the used disposable wearing article from one end toward the other end so that the one end may lie inside and to fix the article in such a rolled up state.

BACKGROUND

Conventionally, disposable wearing articles are known including tape tabs used to roll up used wearing articles and to fix the articles in such a rolled up state. For example, Patent Literature 1 discloses a disposable wearing article including a tape tab formed of tape base material partially provided with mechanical hooks.

CITATION LIST

Patent Literature

{PTL 1}: JP H10-137008 A

SUMMARY

Technical Problem

According to the wearing article disclosed in Patent Literature 1, the tape basic material is formed of a nonwoven fabric having a mechanical hook area provided with the mechanical hooks and an exposed area in which none of the mechanical hooks is provided and the nonwoven fabric is exposed. Before use, such tape tab is folded back on itself with the mechanical hook area inside so that the mechanical hook area may face the exposed area and the mechanical hooks may intertwine with fibers of the nonwoven fabric defining the exposed area. In this way, the mechanical hooks and the fibers are interlinked with each other to keep the tape tab in the folded back state. For disposal of the used disposable wearing article, the wearing article may be rolled up with one end of the article inside and the other end outside and then the article may be fixed in such a rolled up state by the mechanical hooks of the tape tab. Specifically, the mechanical hook area and the exposed area may be released from the interlocking relationship to develop the tape tab from the folded back state and then the mechanical hooks may be fastened to the wearing article itself to prevent the rolled up wearing article from being unintentionally unrolled. In this way, the used wearing article can be held compact for disposal without an anxiety that body waste within the wearing article might be exposed outside.

However, the mechanical hook area as described above is fully interlinked with the exposed area and, in consequence, it is required to release the mechanical hook area and the exposed area from the interlocking relationship by pulling the mechanical hook area upward, to develop these two areas from each other and to fasten the mechanical hook area to the wearing article itself at a desired position thereof. In the case of this Patent Literature 1, it is required to pull the mechanical hook area upward to develop the mechanical area and the exposed area from each other and consequently a series of handling to fasten the used wearing article in the rolled up state may correspondingly include extra step or steps causing the user to be bothered.

An object of the present invention is to improve the conventional wearing article, thereby providing a disposable wearing article including the tape tab capable of fastening the used disposable wearing article in a simple way.

Solution to Problem

The present invention relates to an improvement in a disposable wearing article having a longitudinal direction and a transverse direction being orthogonal thereto and including a chassis having a skin-contact surface and a non-skin-contact surface lying on a side opposite to the skin-contact surface and a tape tab attached to the non-skin-contact surface.

In the disposable wearing article as described above, the present invention lies in that the tape tab is formed of a fibrous nonwoven fabric and includes a first section provided with hooks of a mechanical fastener, a second section lying between the first section and the chassis and a fold lying between the first and second sections wherein the first section and the second section are folded back along the fold with the mechanical fastener inside; the first section has a fastening portion at least partially provided with the mechanical fastener, an intermediate portion extending between the fastening portion and the fold and a finger grip portion located on the side opposite to the intermediate portion of the fastening portion wherein the intermediate portion and the finger grip portion are provided with a first temporary joint spots and a second temporary joint spots, respectively, functioning to join the first section and the second section to each other temporarily; and the mechanical fastener is kept in the state being not retained in the second section.

Advantageous Effects of Invention

According to one or more embodiments of the present invention, the first section and the second section are temporarily joined to the finger grip portion and the intermediate portion. Merely by pulling the temporary joint spots to disable the temporary joint function, the first section can be developed from the second section and, for this reason, the mechanical fastener in the first section can be easily retained on the other sections.

BRIEF DESCRIPTION OF DRAWINGS

{FIG. 1}

{FIG. 2}

{FIG. 3}

{FIG. 4}

{FIG. 5}

{FIG. 6} FIG. 6 (a) is a perspective view illustrating the disposable diaper in a rolled up state and FIG. (b) is a perspective view illustrating the disposable diaper fastened by a tape tab in the rolled up state.

{FIG. 7}

DESCRIPTION OF EMBODIMENTS

Figure 1:
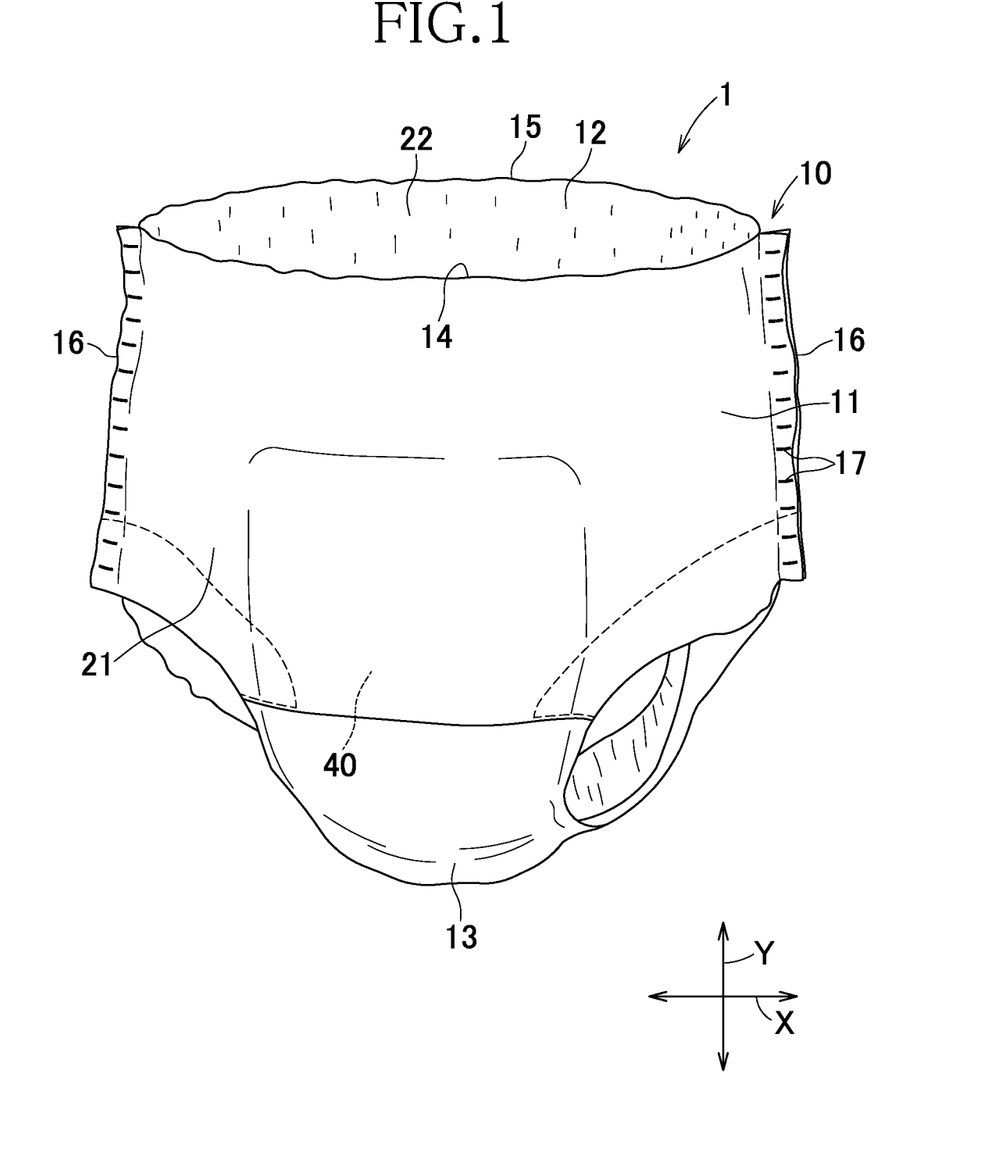
FIG. 1 is a perspective view of a disposable diaper as an example of the disposable wearing article according to the present invention as viewed from a front waist region side.
Figure 2:
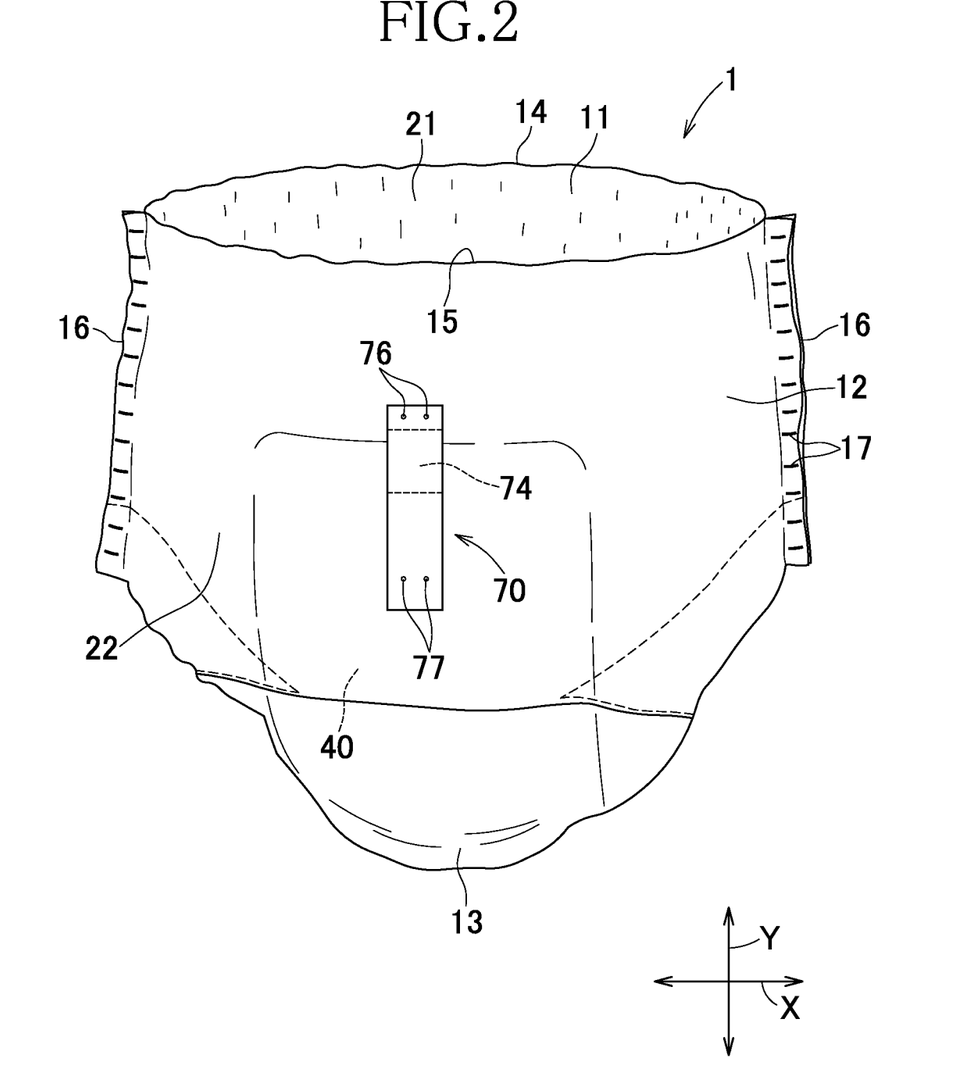
FIG. 2 is a perspective view of the disposable diaper as viewed from a rear waist region side.

Referring to FIGS. 1 and 2, a disposable diaper 1 has skin-contact surface and non-skin-contact surface which is opposite to the skin-contact surface and includes a chassis 10, an absorbent structure 40 placed on the skin-contact surface of the chassis 10 and a tape tab 70 attached to the non-skin-contact surface of the chassis 10. The chassis 10 has a front waist region 11, a rear waist region 12, a crotch region 13 extending between the front and rear waist regions 11, 12, front and rear end edges 14, 15 extending in a transverse direction X and both side edges 16 extending in a longitudinal direction Y. The tape tab 70 extends in the longitudinal direction Y on the non-skin-contact surface of the rear waist region 12. The both side edges 16 are formed with tearable seams 17 continually extending in the longitudinal direction Y through which the front and rear waist regions 11, 12 are coupled to each other so that the front and rear end edges 14, 15 may define a waist-opening and the both side edges 16 in the crotch region 13 may define leg-openings. When it is necessary to take off the diaper 1 from the wearer's body, the wearer him- or herself or the care person may grip, with the respective hands, portions of the front and rear waist regions 11, 12 in vicinities of the seams and forcibly pull these waist regions 11, 12 in opposite directions to separate these waist regions from each other.

Figure 3:
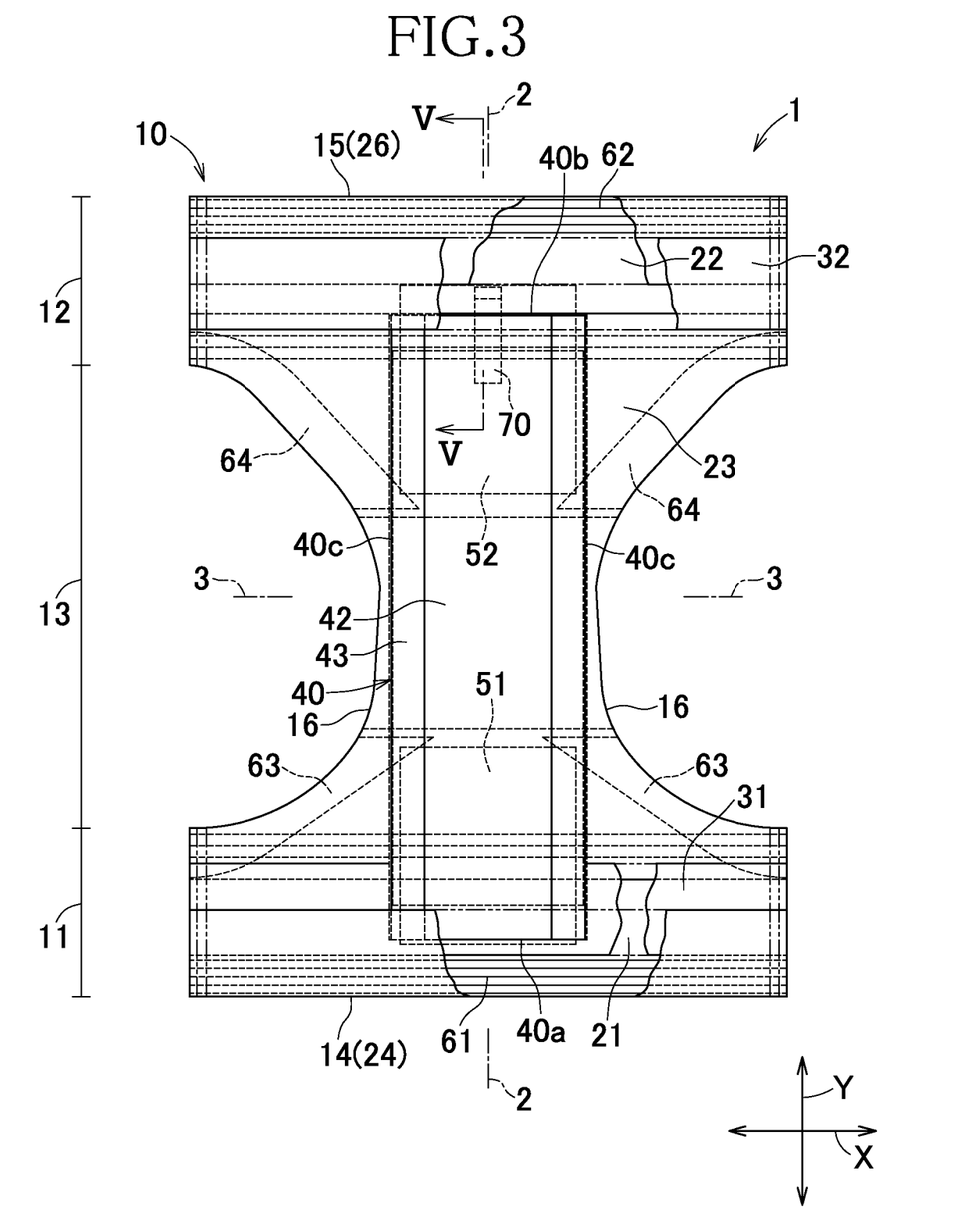
FIG. 3 is a partially cutaway developed view of the disposable diaper.
Figure 4:
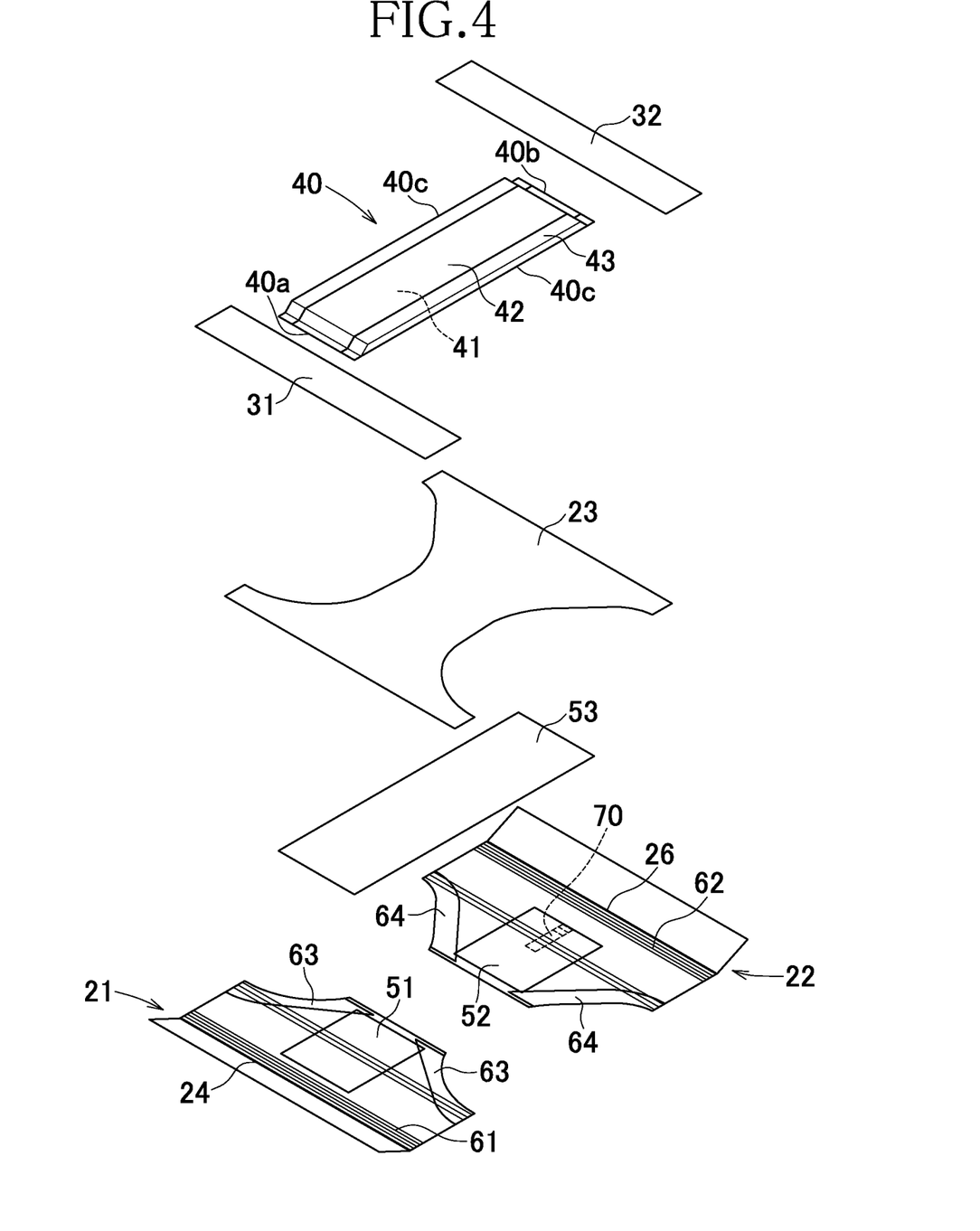
FIG. 4 is an exploded perspective view of the disposable diaper.

Referring to FIGS. 3 and 4, the diaper 1 has an imaginary longitudinal center line 2-2 bisecting a dimension in the transverse direction X and an imaginary transverse center line 3-3 bisecting a dimension in the longitudinal direction Y about which the diaper 1 is symmetric. These FIGS. 3 and 4 illustrate respective elastic elements under tension against a contractile force thereof.

The chassis 10 includes inelastic front and rear waist sheets 21, 22 defining the front and rear waist regions 11, 12, respectively, an inelastic base sheet 23 coupling the front and rear waist sheets 21, 22 with each other and defining the crotch region 13, a first elastic sheet 31 placed in the front waist region 11, and a second elastic sheet 32 placed in the rear waist region 12. The absorbent structure 40 is placed on the interior side of the front and rear waist sheets 21, 22 and the base sheet 23.

As material for the front and rear waist sheets 21, 22 and the base sheet 23, for example, a heat-sealble spunbond fibrous nonwoven fabric may be used having a mass per unit area in a range of about 10 to about 40 g/m2, preferably in a range of about 13 to about 20 g/m2 and a fiber density in a range of about 0.03 to about 0.10 g/cm3, preferably in a range of about 0.04 to about 0.09 g/cm3.

The first and second elastic sheets 31, 32 have an elongate shape and extend in the transverse direction X between the both side edges 16 of the first and second waist regions 11, 12, respectively. As material for the first and second elastic sheets 31, 32, for example, elastic fibrous nonwoven fabrics made of heat-sealable elastomer fibers may be used having a mass per unit area in a range of about 20 to about 50 g/m2, preferably in a range of about 30 to about 40 g/m2 and a fiber density in a range of about 0.01 to about 0.04 g/cm3, preferably in a range of about 0.025 to about 0.035 g/cm3. Specifically, the first and second elastic sheets 31, 32 may include fibers made of a mixture of thermoplastic polyurethane polymers and thermoplastic polymers other than the thermoplastic polyurethane polymers, for example, styrene elastomer, polyolefin elastomer, vinyl chloride elastomer, amide elastomer, polyethylene, polypropylene, or polyolefin polymer such as polystyrene polymers. These first and second elastic sheets 31, 32 are elastically stretchable and contractible at least in the transverse direction X.

The first elastic sheet 31 overlaps a front end portion 40a of the absorbent structure 40 on a bottom surface thereof and is contractibly attached to this front end portion 40a under tension in the transverse direction X. The front waist sheet 21 is folded along a fold line 24 extending in the transverse direction X toward the imaginary transverse center line 3-3 so as to cover the front end portion 40a of the absorbent structure 40 and, in addition, to overlap the first elastic sheet 31. The fold line 24 defines the front end portion 14 of the diaper 1.

The front waist sheet 21 is disposed with a plurality of strand- or string-like elastic elements 61 contractibly secured thereto under tension in the transverse direction X. The first elastic sheet 31 cooperates with the elastic elements 61 to elasticize the front waist region 11 in the transverse direction X, thereby assuring the front waist region 11 to be kept in close contact with the wearer's body. More specifically, the first elastic sheet 31 assures the diaper 1 to be kept in close contact with the wearer's ventral region and the elastic elements 61 assure the diaper 1 to be kept in close contact with the wearer's waist and thereby prevent body exudates from leaking out through the waist-opening.

The second elastic sheet 32 overlaps a rear end portion 40b of the absorbent structure 40 on an absorbent surface thereof and is contructibly attached to this rear end portion 40b under tension in the transverse direction X. The rear waist sheet 22 is folded inward in the longitudinal direction Y along a fold line 26 extending in the transverse direction X so as to overlap the second elastic sheet 32. The fold line 26 defines the rear end portion 15 of the diaper 1.

The rear waist sheet 22 is disposed with a plurality of strand- or string-like elastic elements 62 contractibly secured thereto under tension in the transverse direction X. The second elastic sheet 32 cooperates with the elastic elements 62 to elasticize the rear waist region 12 in the transverse direction X, thereby assuring the rear waist region 12 to be kept in close contact with the wearer's body. More specifically, the second elastic sheet 32 assures the diaper 1 to be kept in close contact with the wearer's ventral region and the elastic elements 62 assure the diaper 1 to be kept in close contact with the wearer's waist, thereby preventing body waste from leaking out through the waist-opening.

Each of the front and rear waist sheets 21, 22 defining each of the leg-openings is disposed with a pair of tape-like elastic elements 63, 63 or 64, 64 contractibly secured thereto under tension. As material for these elastic elements 63, 64, an elastic fibrous nonwoven fabric formed of heat-sealable elastomer fibers may be use having a mass per unit area in a range of about 20 to about 50 g/m2, preferably in a range of about 30 to about 40 g/m2 and a fiber density in a range of about 0.01 to about 0.04 g/cm3, preferably in a range of about 0.025 to about 0.35 g/cm3. Specifically, the first and second elastic sheets 31, 32 may include a mixture of thermoplastic polyurethane polymers and thermoplastic polymers other than the thermoplastic polyurethane polymers, for example, styrene elastomer, polyolefin elastomer, vinyl chloride elastomer, amide elastomer, polyethylene, polypropylene or polyolefin polymers such as polystyrene polymers. In this regard, such elastic fibrous nonwoven fabric may be subjected to a stretching treatment to improve the elasticity thereof. For such stretching treatment, for example, it is possible to use the well known stretching treatment adapted to pass the elastic fibrous nonwoven fabric pass between a pair of gears, thereby forming the elastic nonwoven fabric with further stretched regions and not further stretched regions.

Leakage-barrier sheets 51, 52 are layered on interior surfaces of the front and rear waist sheets 21, 22, respectively. As material for the leakage-barrier sheets 51, 52, for example, an air-permeable but liquid-impermeable plastic film may be used. On the interior surfaces of the leakage-barrier sheets 51, 52, an additional leakage-barrier sheet 53 is layered so that the front and rear waist sheets 21, 22 may be joined to each other in the longitudinal direction Y by the intermediary of this leakage-barrier sheet 53. As material for the leakage-barrier sheet 53, an air-permeable but liquid-impermeable plastic film or a laminate composed of such film and fibrous nonwoven fabric may be used. The leakage-barrier sheets 51, 52, 53 are arranged so as to overlap the absorbent structure 40.

The absorbent structure 40 has a vertically long rectangular shape defined by front and rear ends 40a, 40b extending in the transverse direction X and both side edges 40c extending in the longitudinal direction Y. The absorbent structure 40 extends across the crotch region 13 and further into the front and rear waist regions 11, 12 so that the front end 40a may lie in the front waist region 11 and the rear end 40b may lie in the rear waist region 12.

The absorbent structure 40 includes an absorbent body 41 formed of any absorbent core, for example, including a mixture of fluff pulp and superabsorbent polymer particles and wrapped with a liquid-diffusive sheet (not shown), a body-side liner 42 covering an absorbent surface of the absorbent body 41 and a pair of cover sheets 43 adapted to cover the both side edge regions of the absorbent body 41 from a bottom surface thereof and folded toward the absorbent surface.

Figure 5:
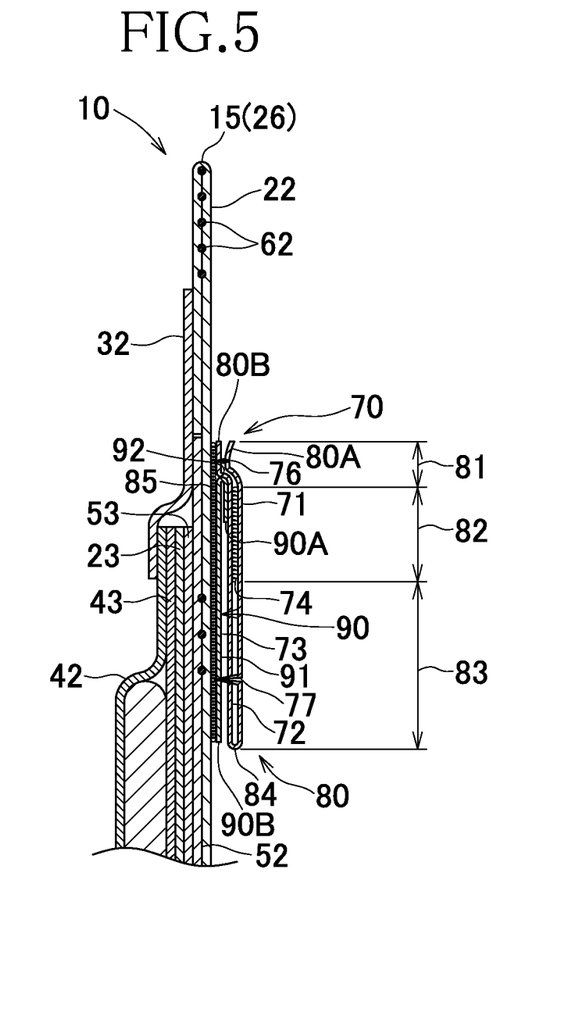
FIG. 5 is a scale-enlarged sectional view taken along line V-V in FIG. 3.

Referring to FIG. 5, the tape tab 70 is attached to the rear waist sheet 22. The tape tab 70 includes a first section 71, a second section 72 and a third section 73 successively disposed in this order and respectively extend in the longitudinal direction Y. The second section 72 lies on the interior side of the first section 71, a fold 84 is formed between the first section 71 and the second section 72 along which these sections 71, 72 are contiguous to each other and folded so as to overlap each other. The third section 73 lies on the interior side of the second section 72 and is joined to the second section 72. Consequently, the first, second and third sections 71, 72, 73 successively disposed in this manner has a cross-sectional surface in Z-shape.

The first section 71 and the second section 72 are formed of a first tape element 80 made of a fibrous nonwoven fabric. The first tape element 80 has a first end portion 80A opposite to the fold 84 in the longitudinal direction Y on the side of the first section 71 and a second end portion 80B lying l on the side of the second section 72 in side-by-side relationship with the first end portion 80A. In consequence, the first and second end portions 80A, 80B point to the rear end portion 15 and lie between the fold 84 and the rear end portion 15.

The first section 71 includes a finger grip portion 81 defined by the first end portion 80A, a fastening portion 82 lying adjacent to the finger grip portion 81 and provided with a mechanical fastener 74 and an intermediate portion 83 extending between the fastening portion 82 and the fold 84. The mechanical fastener 74 is arranged on a surface facing the second section 72. In the vicinity of the second end portion 80B, the second section 72 extends in the longitudinal direction Y beyond the third section 73 and secured to the rear waist sheet 22 in a joining area 85.

The third section 73 is formed of a second tape element 90 made of a fibrous nonwoven fabric and has a fastening area 91 joined to the rear waist sheet 22, a first end portion 90A lying adjacent to the first and second end portions 80A, 80B, folded back toward the side of the first region 71 and joined to the second region 72, a second end portion 90B lying on the side of the fold 84, and a fold 92 along which a fastening area 91 and the first end portion 90A are joined to each other. The first end portion 90A and the fastening area 91 are folded along the fold 92 and overlap each other. With the first end portion 90A and the fastening area 91 having been folded in this manner, the first and second end portions 90A, 90B lie at least on the side of the crotch region 13 with respect to the fold 92. The fastening area 91 extends to the vicinity of the fold 84 of the first tape element 80 and is permanently secured to the rear waist sheet 22 in the joining area 85.

<Measuring Method for Tensile Strength of First and Second Tape Elements>

Tensile strength of the second tape element 90 is set to be higher than that of the first tape element 80. Tensile strength was measured with the use of AUTOGRAPH Tensile Tester manufactured by Shimadzu Corporation in Japan. As test pieces, the first and second tape elements 80, 90 are respectively cut out from the tape tab 70 and cut-width (mm) thereof measured. With one side edge of the test piece held by one of chucks and the other side edge held by the other chuck, these chucks were distanced from each other at a tension rate of 100 mm/min and a peel angle of 180° and a strength at breakage was measured. Based on the measured width of the test piece (mm), tensile strength per width of 100 mm (N/10 mm width) of each test piece was calculated and the tensile strength of the first tape element 80 was compared with the tensile strength of the second tape element 90.

Figure 6:
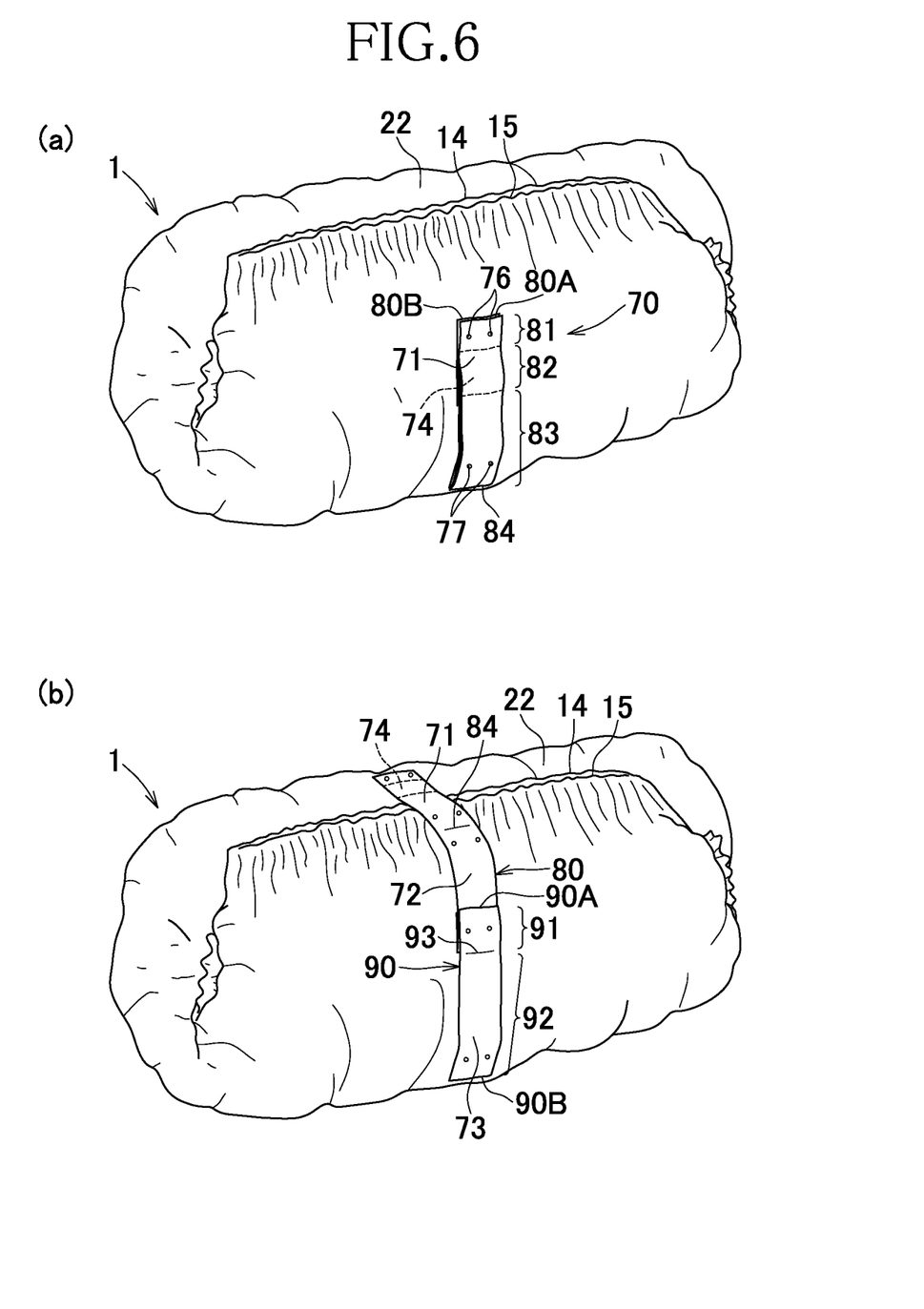

Referring to FIG. 6, the above-mentioned tape tab 70 is provided with, on the outer side of the mechanical fastener 74 as viewed in the longitudinal direction Y, dot-like first and second temporary joint spots 76, 77. Specifically, a plurality of the first temporary joint spots 76 and a plurality of the second temporary joint spots 77 are respectively arranged in a width direction of the tape tab 70, i.e., in the transverse direction X of the tape tab 70. Referring again to FIG. 5, the first temporary joint spots 76 temporarily join the finger grip portion 81 in the first section 71 and the first end portion 80B of the second section 72 with each other and these first temporary joint spots 76 are respectively aligned in the thickness direction of the respective spots. The second temporary joint spots 77 temporarily join an intermediate portion 83 of the first section 71, the second section 72 and the fastening area 91 of the third sections 73 together and these second temporary joint spots 77 are respectively aligned in the thickness direction of the respective spots. These first and second temporary joint spots 76, 77 may be formed with the use of pin embossing and, more specifically, the tape tab may be pressed by heated boss (pin) from the first section 71 toward the second section to heat-seal the heat-sealable fibers in the respective sections.

As material for the first tape element 80, for example, a spunbond fibrous nonwoven fabric may be used having a mass per unit area in a range of about 40 to about 100 g/m2, preferably in a range of about 60 to about 80 g/m2 and, as material for the second tape element 90, a spunbond fibrous nonwoven fabric may be used having a mass per unit area in a range of about 20 to about 60 g/m2, preferably in a range of about 30 to about 50 g/m2. Such fibrous nonwoven fabric at least partially contains therein heat-sealable fibers making it possible to be heat-sealed in the first and second temporary joint spots 76, 77, respectively. As the heat-sealable fibers, for example, a synthetic fiber containing polyolefin-polymer such as polyethylene, polypropylene and polystyrene may be used.

While the mechanical fastener 74 in the first section 71 faces the second section 72, hook elements of the mechanical fastener 74 are not easily caught by fibers of the first tape element 80 since a fiber confounding and/or a heat sealing density of the first tape element 80 defining the second section 72 is higher than that in the front and rear waist sheets 21, 22 formed of a flexible fibrous nonwoven fabric and, consequently, loop elements sufficient to catch the mechanical fastener 74 are not formed. Thus, the mechanical fastener 74 has substantially no retaining function for the second section 72. An average value of the peel strength between these mechanical fasteners 74 and the second section 72 is in a range of about 0 to about 0.4 N, preferably in a range of about 0.05 to about 0.2 N. Here, the average peel strength may include 0 (zero). In other words, the mechanical fastener 74 which is not retained at all in the second section 72 may be acceptable. The average peel strength was measured by the method as will be described below.

<Measuring Method for Average Peel Strength of Mechanical Fastener>

Average peel strength was measured with the use of AUTOGRAPH Tensile Tester manufactured by Shimadzu Corporation. Using the tape tab 70 cut off from the diaper 1 was used as test piece, the first end portion 80A of the first section 71 was held by one of a pair of chucks, the second end portion 80B of the second section 72 was held by the other and these chucks were distanced from each other at a tension rate of 100 mm/min and at a peel angle of 180° to measure the peel strength. More specifically, the measurement was started by disabling the temporary joint function provided by the first temporary joint spot 76 between the first section 71 and the second section 72, moving the chucks to a position just before the mechanical fastener 74 would be spaced apart from the second section 72 and the measurement was ended by moving the chucks to a position at which the mechanical fastener 74 were fully distanced from the second section 72. An average value calculated from the peel strength values obtained by this measurement was recorded as the average peel strength in the present embodiment.

If the first section 71, the second section 72 and the third section 73 are not retained each other during a process (not shown) of attaching the tape tab 70 to the chassis 10 or during a process (not shown) of conveying this assembly, there is a possibility that the first section 71 and the second section 72 might be curled off from the third section 73 and caught by manufacturing apparatuses or the other structures. To avoid this, the first section 71 and part of the second section 73 may be reliably engaged with each other by the intermediary of the first temporary joint spots 76. In a similar fashion, the first section 71, the second section 72 and part of the third section 73 may be reliably retained in engagement with each other by the intermediary of the second temporary joint spots 77.

In the diaper 1 as has been described above, the tape tab 70 may keep a state in which the first section 71, the second section 72 and the third section 73 are temporarily joined and lapped with each other/unless the first and second temporary joint spots 76, 77 of the tape tab 70 are intentionally disabled to peel the first section 71 and the second section 72 off from each other. For this reason, there is no anxiety that the first and second temporary joint spots 76, 77 might be unintentionally disabled, in consequence, the first section 71 and the second section 72 might spread out and the mechanical fastener 74 might be caught by clothes or the like. The peel strength between the second and third section 72, 73 in the second temporary joint spots 77 is set to be lower than the peel strength between the first and second sections 71, 72 in the first temporary joint spots 76. To lower the peel strength between the second and third sections 72, 73 in the second temporary joint spots 77, for example, a mass of the second tape element 90 defining the third section 73 may be set to be smaller than that of the first tape element 80 defining the second section 72.

<Measuring Method for Peel Strength of Temporary Joint Spots>

Peel strength was measured with the use of AUTOGRAPH Tensile Tester manufactured by Shimadzu Corporation in Japan. Using the tape tab 70 cut off from the diaper 1 was used as test piece, the first end portion 80A of the first section 71 was held by one of a pair of chucks, the second end portion 80B of the second section 72 was held by the other and these chucks were distanced from each other at a tension rate of 100 mm/min and at a peel angle of 180° to measure the peel strength. When a peel strength of the first temporary spots 76 was measured, the retaining effect of the mechanical fastener 74 in the second section 72 as well as the retaining effect of the first through the third sections 71 through 73 in the second temporary joint spots 77 were disabled to conduct the measurement. In a similar manner, when a peel strength between the second and third sections 72, 73 in the second temporary joint spots 77 was measured, the retaining effect of the first section 71 and the second section 72 in the first temporary joint spots 76, the retaining effect of the mechanical fastener 74 and the second section 72 as well as the retaining effect of the first section 71 and the second section 72 in the second temporary spots 77 were disabled to conduct the measurement.

For disposal of the used diaper 1, the crotch region 13 may be rolled up toward the front and rear waist regions 11, 12 as illustrated in FIG. 6 (*a*). During this handling, the tape tab 70 is kept in a folded up state unless the tape tab is intentionally peeled off. As illustrated in FIG. 6 (*b*), it is possible to fix the used diaper in the state rolled up with the use of the tape tab 70. Specifically, the temporary joint effect of the first and second temporary joint spots 76, 77 is disabled, the first section 71 and the second section 72 are peeled off from the third section 73 and spread out, and the mechanical fastener 74 was fastened to the rear waist sheet 22 or the base sheet 23 of the rolled up diaper 1. The mechanical fastener 74 faces the non-skin-contact surface of the diaper 1, may be fastened to the rear waist sheet 22 and, in consequence, it is possible to fix the diaper 1 in rolled up state.

Figure 7:
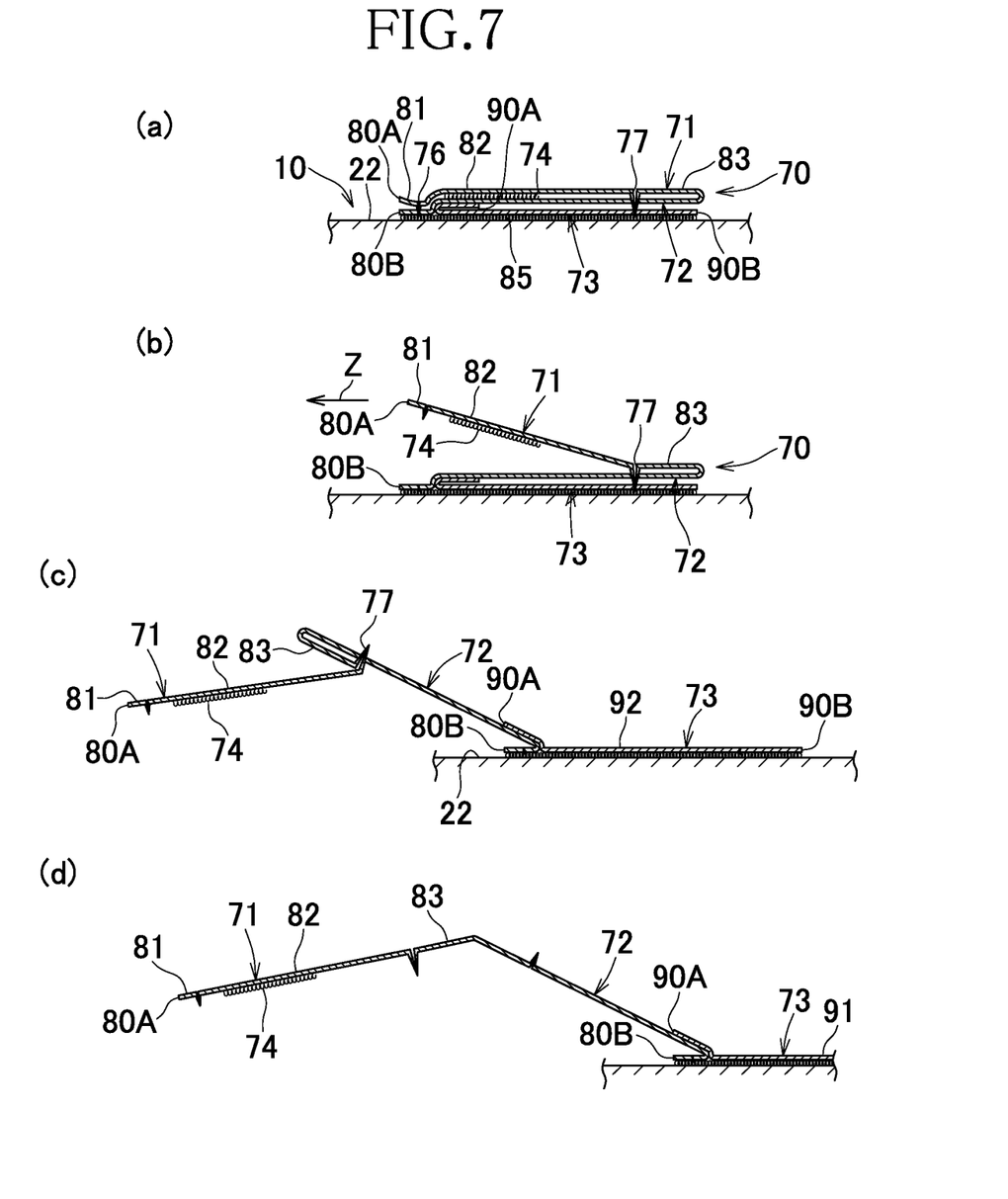
FIG. 7(a) through FIG. 7(d) are diagrams illustrating sequential movements of the tape tab.

Referring to FIG. 7 (*a*), the finger grip portion 81 may be pinched with the fingers and tipped to develop it. The finger grip portion 81 is provided at a position distanced inward from the first end portion 80A with the first temporary joint spots 76 and consequently the first end portion 80A is sufficiently distanced from the second section 72 to pinch the first end portion 80A without any effort. With the finger grip portion 81 pinched in this manner, the temporary joint effect of the first temporary joint spots 76 may be disabled to peel to peel the finger grip portion 81 and the fastening portion 82 in the first section 71 off from the second section 72. While the fastening portion 82 is provided with the mechanical fastener 74, the mechanical fastener 74 are not substantially retained in the second section 72 facing the mechanical fastener 74 and consequently the fastening portion 82 is peeled off from the second section 72 when the first temporary joint spots 76 are disabled.

Referring to FIG. 7 (*b*), the finger grip portion 81 may be pulled in a direction indicated by an arrow toward the crotch region 13 beyond the rear end portion 14 of the rolled up diaper 1 until the second temporary joint spot 77 is partially disabled to peel the first and second sections 71, 72 off from the third section 73. The mechanical fastener 74 is substantially not retained in the second section 72 and the second section 72 also is not retained in the third section 73 except the temporary joint spot. In consequence, the first and second sections 71, 72 may be easily peeled off from the third section 73. The peel strength between the second and third sections 72, 73 of the second temporary joint spot 77 is lowered from that the first temporary joint spot 76 and the second section 72 is further easily peeled off from the third section 73.

When the finger grip 81 is further pulled from the position in FIG. 7 (c), the second temporary joint spots 77 of the first section 71 and the second section 72 are disabled in the intermediate portion 83 and these first and second sections 71, 72 are peeled off as illustrated in FIG. 7 (d). When the second temporary joint spot 77 are disabled, the first section 71, the second section 72 and the third section 73 spread substantially in aligned in a straight line. When these three sections spread in a straight line, the mechanical fastener 74 faces the non-skin-contact surface of the rolled up diaper 1 and may be easily retained on the rear waist sheet 22.

For the tape tab 70 according to this embodiment, it is possible to develop the tape tab 70 from its folded state merely by pulling the finger grip portion 81 toward the side of the rear end portion 15 and then to retain the mechanical fastener 74 on a desired position on the non-skin-contact surface of the diaper 1. In this way, it is possible to develop the tape tab 70 and to retain on the non-skin-contact surface of the diaper 1 without any additional handling to peel the first section 71 off from the second section 72. Consequently, the used diaper 1 can be easily fastened in a rolled up state without being bothered with a series of handling.

The mechanical fastener 74 is substantially not retained in engagement with the fibers of the second section 72 facing the mechanical fastener 74 and the first and second sections 71, 72 may be easily peeled off from each other after the first and second temporary joint spots 76, 77 have been disabled. In this way, it is unnecessary to pull the first section 71 significantly in order to peel these sections off from each other. In addition, the first and second temporary joint spots 76, 77 are located on the outer side of the mechanical fastener 74 as viewed in the longitudinal direction Y of the mechanical fastener 74 so that these temporary joint spots might not overlap the mechanical fastener 74. With such arrangement, it is possible to prevent the mechanical fastener 74 from being caught by the second section 72.

In this regard, it is not essential to arrange the first and second temporary joint spots 76, 77 out of overlapping with the mechanical fastener 74 and it is possible to arrange these temporary joint spots so as to overlap the mechanical fastener 74. Here, it is desired to arrange the first and second temporary joint spots 76, 77 without a possibility that the mechanical fastener 74 might be retained in the second section 72.

The second tape element 90 has the first end portion 90A and the fastening portion 91, the upper surface of the first end portion 90A is joined to the first tape element 80 defining the second section 72 and the lower surface of the fastening portion 91 is joined to the rear waist sheet 22. In addition to the respective joints, the permanent joint of the second end portion 80B of the second section 72 to the rear waist sheet 22 makes it possible to deconcentrate the peel strength generated when the second section 72 is pulled. Referring to FIG. 7 (c), while the second end portion 80B joined to the rear waist sheet 22 is subjected to a relatively large peel strength when the tape tab 70 is developed at one handling, i.e., pulling the finger grip portion 81, it is possible to prevent the second end portion 80B from being peeled off from the rear waist sheet 22 since the second tape element 90 are continuously joined to the second section 72, the second end portion 80B and the rear waist sheet 22. The first tape element 80 is subjected to a large peel strength when the finger grip portion 81 is pulled as described above and there is a possibility that the first tape element 80 might be broken. However, it is possible to avoid such anxiety by forming the first tape element 80 from a fibrous nonwoven fabric having a tensile strength higher than that of the second tape element 90. While the fibrous nonwoven fabric having a relatively high tensile strength tends to have a correspondingly higher stiffness in comparison to the fibrous nonwoven fabric having a relatively low tensile strength, the fibrous nonwoven fabric having the high tensile strength may be used only for the first tape element 80 and the fibrous nonwoven fabric having the low tensile strength may be used to prevent the stiffness of the tape tab 70 as a whole from being increased.

Referring again to FIGS. 7 (c) and 7 (d), in the first section 71, the second section 72 and the third section 73 temporarily joined to each other by the intermediary of second temporary joint spot 77, first, the second section 72 and the third section 73 are separated from each other and then the first section 71 and the second section 72 are separated. However, it is possible to arrange these sections so that these sections may be separated from each other in the reverse sequence. Specifically, first, the first section 71 and the second section 72 may be separated from each other and then the second section 72 and the third section 73 may be separated from each other. It is also possible to arrange these sections so that these sections may be separated from each other at once.

According to this embodiment, the rear waist sheet 22 lying on the non-skin-contact surface of the chassis is formed of the fibrous nonwoven fabric on which the mechanical fastener 74 can be retained and consequently it is possible to retain the mechanical fastener 74 at any position on the rear waist sheet 22. In view of this, even when the diaper 1 has absorbed a large amount of body exudates such as urine and the absorbent body 41 has been swollen, it is reliably possible to fix the diaper 1 in a rolled up state.

The cover sheet 43 defines the non-skin-contact surface in the crotch region 13. When it is tried to roll up the diaper 1 and to fix the rolled up diaper 1 with the use of the tape tab 70, it is conceivable that the mechanical fastener 74 may face the crotch region 13. In view of this, the cover sheet 43 is preferably formed of a laminate composed of a plastic film and a fibrous nonwoven fabric so that the fibrous nonwoven fabric may lie on the non-skin-contact surface. To facilitate the mechanical fastener 74 to be engaged with this fibrous nonwoven fabric, as the fibrous nonwoven fabric, for example, a heat-sealable spunbond fibrous nonwoven fabric may be used having a mass per unit area in a range of about 10 to about 40 g/m2, preferably in a range of about 13 to about 20 g/m2 and a fiber density in a range of about 0.03 to about 0.10 g/cm3, preferably in a range of about 0.04 to about 0.09 g/cm3. An arrangement such that the mechanical fastener 74 may be retained on not only on the rear waist sheet 22 but also on the leakage-barrier sheet 53 is preferable to broaden an area in which the mechanical fastener 74 may be retained, thereby fixing the diaper 1 in a rolled up state reliably.

While a joint spot in which the second end portion 80B of the second section 72 is joined to the rear waist sheet 22 is continuous with a joint region in which the fastening portion 91 of the third section 73 is joined to the rear waist sheet 22 according to this embodiment, these joint regions may be arranged so as to be discontinuous, i.e., distanced from each other in the longitudinal direction Y.

While the tape tab 70 including the first section 71, the second section 72 and the third section 73 has been described hereinabove according to this embodiment, it is possible to form the tape tab 70 from the first section 71 and the second section 72 without the third section 73. Here, a substantially entire surface of the second section 72 may be joined directly to the rear waist sheet 22 by the intermediary of a joint spot. In this regard, the tape tab 70 including the first, second and third sections and folded back in a Z-shape is preferable from the viewpoint of various advantageous aspects such that a large dimension of the tape tab in a developed state is ensured, the mechanical fastener 74 are reliably retained on the non-skin-contact surface of the chassis and the diaper 1 is easily fixed in its rolled up state. While the first section 71 and the second section 72 have been described to be formed of the single first tape element 80 and the third section 73 has been described to be formed of the separately prepared second tape element 90, it is possible to form these first section 71, the second section 72 and the third section 73 from one and the same fibrous nonwoven fabric. Here, a single piece of fibrous nonwoven fabric may be folded in three to define the respective regions.

While the mechanical fastener 74 is arranged substantially entire area of the fastening portion 82 according to this embodiment, it is possible to arrange the mechanical fastener 74 on part of the fastening portion 72 or to arrange a range of the mechanical fastener 74 extending into the finger grip portion 81 and the intermediate portion 83. In other words, the fastening portion 82 may be located between the finger grip portion 81 and the intermediate portion 83 provided with the first and second temporary joint spots 76, 77 and at least a part thereof is provided with the mechanical fastener 74.

While a plurality of the first and second temporary joint spots 76, 77 are respectively arranged so as to be distanced from each other in the transverse direction X according to this embodiment, it is possible to define each of the respective temporary joint spots by a single temporary joint spot. It is also possible to arrange a plurality of the temporary joint spots so as to be distanced from each other in the longitudinal direction Y. In any rate, it is necessary and sufficient condition for the temporary joint spots to be capable of partially and temporarily join the first and second sections 71, 72 and preferably to be capable of easily disabling the temporary joint and to peel the first and second sections 71, 72 off from each other. While the first and second temporary joint spots 76, 77 can be formed heating and pressing the fibrous non-woven fabric, for example, with the use of heat sealing or ultrasonic sealing, it is also possible to form them with the use of the other joining means such as adhesive. In this regard, use of the heat sealing or ultrasonic sealing technique is more preferable than the use of adhesive from the viewpoint that use of the heat sealing or ultrasonic sealing technique makes it possible to form the temporary joint spots aligned with the thickness direction of the first through third sections. The first temporary joint spot 76 is distanced from the first end portion 80A by a range of about 5 to about 30 mm, preferably in a range of about 10 to about 30 mm. Such distance may be set to facilitate the wearer or care person to grip the first end portion 80A.

While the first temporary joint spots 76, 77 are formed only on the tape tab 70, it is possible to provide the tape tab 70 and the chassis 10 with additional temporary joint spots. Specifically, the tape tab 70 temporarily joined to the first and second temporary joint spots 76, 77 during the manufacturing process for the diaper 1 may be layered on the waist sheet 22 to form additional temporary joint spots.

While the first end portion 80A and the second end portion 80B of the first tape element 80 are illustrated to be overlapped each other substantially in alignment with each other, it is possible to arrange these end portions 80A, 80B so that one of them may extend outward in the longitudinal direction Y. Here, the position of the first end portion 80A can be easily recognized and easily gripped. It is also possible to provide the finger grip portion 81 with a visually recognizable area by coloring the finger grip portion 81 differently from the other portions or regions or patterning the finger grip portion 81. The visually recognizable finger grip portion 81 facilitates the finger grip portion 81 to be reliably gripped and thereby assures that the finger grip portion 81 may be merely pulled to develop the tape tab 70 easily.

While the first end portion 90A and the second end portion 90B of the second tape element 90 are illustrated to overlap each other out of alignment in the longitudinal direction Y, it is possible to arrange these two end portions overlapping each other substantially aligned with each other.

While the tape tab 70 is arranged so as to extend along the imaginary longitudinal center line 2-2 according to this embodiment, it is also possible to arrange the tape tabs in the vicinity of the side edges 16 of the front waist region 11 or the rear waist region 12. It is also possible to arrange the tape tab 70 so as to extend in the transverse direction X. When the tape tabs 70 are arranged in the vicinity of the side edges 16 so as to extend in the transverse direction X, these tape tabs 70 may be developed and used for disposal of the wearing article and used also for size-adjustment of a waist size of the wearing article on the wearer's body.

The disclosure of the present invention described heretofore may be arranged at least as follows:

The disposable wearing article 1 has the longitudinal direction Y and the transverse direction X being orthogonal thereto and includes the chassis 10 having the skin-contact surface and the non-skin-contact surface lying on the side opposite to the skin-contact surface and the tape tab 70 attached to the non-skin-contact surface.

In the disposable wearing article 1 described just above, the present invention includes the aspects as described below:

The tape tab 70 is formed of the fibrous nonwoven fabric and includes the first section 71 provided with the hooks of the mechanical fastener 74 of the mechanical fastener, the second section 72 lying between the first section 71 and the chassis 10 and the fold 84 lying between the first and second sections 71, 72. The first section 71 and the second section 72 are folded back along the fold 84 with the mechanical fastener 74 inside.

The first section 71 has the fastening portion 82 at least partially provided with the mechanical fastener 74, the intermediate portion 83 extending between the fastening portion 82 and the fold 84 and the finger grip portion 81 located on the side opposite to the intermediate portion 83 of the fastening portion 82. The intermediate portion 83 and the finger grip portion 81 are provided with the first temporary joint spots 76 and the second temporary joint spots 77, respectively, functioning to join the first section 71 and the second section 72 to each other temporarily.

The mechanical fastener is kept in the state not retained in the second section.

The present invention as described above may include at least following embodiments:

(1) The first temporary joint spots 76 and the second temporary joint spots 77 are located so as not to overlap the mechanical fastener 74.

(2) The first temporary joint spots 76 and the second temporary joint spots 77 are formed under heat and pressure.

(3) The tape tab 70 further includes a third section 73 layered between the second section 72 and the chassis 10 and one end of the third section 73 is adjacent to the second section 72 and the other end of the third section 73 is joined to the chassis 10.

(4) At least one pair of the first temporary joint spots 76 and the second temporary joint spots 77 are respectively aligned in a thickness direction of the first section 71, the second section 72 and the third section 73 and thereby temporarily join these sections together.

(5) The tape tab 70 has a first tape element 80 formed of a fibrous nonwoven fabric and defining the first and second sections 71, 72 and a second tape element 90 formed of a fibrous nonwoven fabric and defining the third section 73 wherein a tensile strength of the first tape element 80 is set to be higher than that of the second tape element 90.

(6) The second tape element 90 has a first end portion 90A joined to the first tape element 80, a fastening portion 91 fastened to the chassis 10 and a fold 92 lying between the first end portion 90A and the fastening portion 91 so that the second tape element 90 may be folded back along the fold 92.

(7) The tape tab 70 is arranged so that an average peel strength between the mechanical fastener 74 and the second section 72 may be in a range of 0 to 0.4 N.

(8) The chassis 10 has its non-skin-contact surface formed of a fibrous nonwoven fabric capable of retaining the mechanical fastener 74 thereon.

(9) The tape tab 70 is provided on the finger grip portion 81 thereof with a visually recognizable mark.

The respective constituent elements of the disposable diaper 1 are not limited to those described in the present specification but the other various types of material widely used in the relevant technical field may be used without limitation. In this regard, it is also possible to make the diaper 1 from the front waist region 11, the crotch region 13 and the rear waist region 12 continuously arranged in this order.

Terms "first" and "second" used in the specification and claims of the present invention are used merely to distinguish the similar elements, similar positions or the other similar means.

REFERENCE SIGNS LIST 1 diaper (disposable wearing article)
10 chassis
11 front waist region (first or second waist region)
12 rear waist region (first or second waist region)
13 crotch region
70 tape tab
71 first section
72 second section
73 third section
74 mechanical fastener
76 first temporary joint spot
77 second temporary joint spot
80 first tape element
80B second end portion (end portion)
81 finger grip portion
82 fastening area
83 intermediate portion
84 fold
90 second tape element
90A first end portion
90 fastening area
92 fold
X transverse direction
Y longitudinal direction

The invention claimed is:

1. A disposable wearing article having a longitudinal direction and a transverse direction being orthogonal thereto and including a chassis having a skin-contact surface and a non-skin-contact surface lying on a side opposite to the skin-contact surface and a tape tab attached to the non-skin-contact surface, wherein:
the tape tab is formed of a fibrous nonwoven fabric and includes a first section provided with hooks of a mechanical fastener, a second section lying between the first section and the chassis and a fold lying between the first and second sections wherein the first section and the second section are folded back along the fold with the mechanical fastener inside;
the first section has a fastening portion at least partially provided with the mechanical fastener, an intermediate portion extending between the fastening portion and the fold and a finger grip portion located on the side opposite to the intermediate portion of the fastening portion wherein the intermediate portion and the finger grip portion are provided with first temporary joint spots and second temporary joint spots, respectively, functioning to join the first section and the second section to each other temporarily; and
the mechanical fastener is kept in the state being not retained in the second section.

2. The disposable wearing article according to claim 1, wherein the first temporary joint spots and the second temporary joint spots are located so as not to overlap the mechanical fastener.

3. The disposable wearing article according to claim 1, wherein the first temporary joint spots and the second temporary joint spots are formed under heat and pressure.

4. The disposable wearing article according to claim 1, wherein the tape tab further includes a third section layered between the second section and the chassis and one end of the third section is adjacent to the second section and the other end of the third section is joined to the chassis.

5. The disposable wearing article according to claim 4, wherein at least two transversely ones of the first temporary joint spots or the second temporary joint spots are respectively aligned in a thickness direction of the first section, the second section and the third section and thereby temporarily join these sections together.

6. The disposable wearing article according to claim 4, wherein the tape tab has a first tape element formed of a fibrous nonwoven fabric and defining the first and second sections and a second tape element formed of a fibrous nonwoven fabric and defining the third section wherein a tensile strength of the first tape element is set to be higher than that of the second tape element.

7. The disposable wearing article according to claim 6, wherein the second tape element has a first end portion joined to the first tape element, the fastening portion fastened to the chassis and a fold lying between the first end portion and the fastening portion so that the second tape element is folded back along the fold.

8. The disposable wearing article according to claim 1, wherein the tape tab is arranged so that an average peel strength between the mechanical fastener and the second section may be in a range of 0 to 0.4 N.

9. The disposable wearing article according to claim 1, wherein the chassis has a non-skin-contact surface formed of a fibrous nonwoven fabric capable of retaining the mechanical fastener thereon.

10. The disposable wearing article according to claim 1, wherein the tape tab is provided on the finger grip portion thereof with a visually recognizable mark.

11. The disposable wearing article according to claim 2, wherein the first temporary joint spots and the second temporary joint spots are formed under heat and pressure.

12. The disposable wearing article according to claim 2, wherein the tape tab further includes a third section layered between the second section and the chassis and one end of the third section is adjacent to the second section and the other end of the third section is joined to the chassis.

13. The disposable wearing article according to claim 3, wherein the tape tab further includes a third section layered between the second section and the chassis and one end of the third section is adjacent to the second section and the other end of the third section is joined to the chassis.

14. The disposable wearing article according to claim 11, wherein the tape tab further includes a third section layered between the second section and the chassis and one end of the third section is adjacent to the second section and the other end of the third section is joined to the chassis.

15. The disposable wearing article according to claim 12, wherein at least two transversely adjacent ones of the first temporary joint spots or the second temporary joint spots are respectively aligned in a thickness direction of the first section, the second section and the third section and thereby temporarily join these sections together.

16. The disposable wearing article according to claim 13, wherein at least two transversely adjacent ones of the first temporary joint spots or the second temporary joint spots are respectively aligned in a thickness direction of the first section, the second section and the third section and thereby temporarily join these sections together.

17. The disposable wearing article according to claim 14, wherein at least one pair of the first temporary joint spots and the second temporary joint spots are respectively aligned in a thickness direction of the first section, the second section and the third section and thereby temporarily join these sections together.

18. The disposable wearing article according to claim 12, wherein the tape tab has a first tape element formed of a fibrous nonwoven fabric and defining the first and second sections and a second tape element formed of a fibrous nonwoven fabric and defining the third section wherein a tensile strength of the first tape element is set to be higher than that of the second tape element.

19. The disposable wearing article according to claim 13, wherein the tape tab has a first tape element formed of a fibrous nonwoven fabric and defining the first and second sections and a second tape element formed of a fibrous nonwoven fabric and defining the third section wherein a tensile strength of the first tape element is set to be higher than that of the second tape element.

20. The disposable wearing article according to claim 14, wherein the tape tab has a first tape element formed of a fibrous nonwoven fabric and defining the first and second sections and a second tape element formed of a fibrous nonwoven fabric and defining the third section wherein a tensile strength of the first tape element is set to be higher than that of the second tape element.

* * * * *